United States Patent [19]

Guttmann et al.

[11] 4,259,533

[45] Mar. 31, 1981

[54] LIQUID PHASE PROCESS FOR THE MANUFACTURE OF METHYL TERTIARY ETHERS

[75] Inventors: Andrew T. Guttmann, Maple Heights; Robert K. Grasselli, Chagrin Falls, both of Ohio

[73] Assignee: The Standard Oil Company, Cleveland, Ohio

[21] Appl. No.: 71,806

[22] Filed: Sep. 4, 1979

Related U.S. Application Data

[63] Continuation of Ser. No. 697,098, Jun. 17, 1976, abandoned, which is a continuation-in-part of Ser. No. 494,575, Aug. 5, 1974, abandoned.

[51] Int. Cl.³ .............................................. C07C 41/06
[52] U.S. Cl. ..................................................... 568/697
[58] Field of Search ......................................... 568/697

[56] References Cited

U.S. PATENT DOCUMENTS

| | | | |
|---|---|---|---|
| 2,162,913 | 6/1939 | Eversole et al. | 568/694 |
| 2,591,493 | 4/1952 | Arnold et al. | 210/465.2 |
| 2,702,232 | 2/1955 | Arnold et al. | 568/697 X |
| 3,135,807 | 6/1964 | Grasselli et al. | 568/697 |
| 3,285,977 | 11/1966 | Henke et al. | 568/694 |

*Primary Examiner*—Howard T. Mars
*Attorney, Agent, or Firm*—John E. Miller, Jr.; Herbert D. Knudsen; Larry W. Evans

[57] ABSTRACT

The present invention is a homogeneous liquid phase process for the preparation of methyl-t-butyl ether by reacting isobutylene and methanol in the presence of a heteropoly acid of molybdenum, tungsten or vanadium. Other tertiary ethers may be obtained by substituting a different tertiary olefin for isobutylene, e.g. t-amyl methyl ether from 2-methylbutene-2 and methanol.

10 Claims, No Drawings

LIQUID PHASE PROCESS FOR THE MANUFACTURE OF METHYL TERTIARY ETHERS

This is a continuation of application Ser. No. 697,098 filed June 17, 1976, now abandoned, which is a continuation-in-part of application Ser. No. 494,575, filed Aug. 5, 1974, now abandoned.

BACKGROUND OF THE INVENTION

The ether of the invention has been traditionally prepared by the use of a strong mineral acid, e.g. sulfuric acid. Such strong acids under the process conditions are very corrosive and cause significant problems when applied on a commercial scale. As a result, there has been a continuous search for an improved process of high efficiency that avoids these corrosion problems.

Acidic ion exchange resins, which also have been used as catalysts for the preparation of the ethers of the invention, cannot be used at temperatures higher than 70°–75° C. due to their poor thermal stability. This limitation results in long reaction times and low throughput per unit volume of a reaction vessel.

Another problem associated with the known processes is the formation of undesirably large quantities of dimethyl ether. The present invention also deals with this problem and substantially reduces the amount of this undesirable by-product.

SUMMARY OF THE INVENTION

The present invention is a process for the preparation of methyl-t-alkyl ethers comprising reacting in the liquid phase a mixture of a tertiary olefin of the formula $RHC=CR_2^1$, wherein R is H or alkyl, and $R^1$ is alkyl, and methanol in the presence of a homogeneous free-heteropolyacid catalyst having the formula:

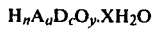

$$H_nA_aD_cO_y \cdot XH_2O$$

wherein
A is P, B, Si, Ge, Sn, As, Sb, U, Mn, Re, Cu, Ni, Co, Fe, Ce, Th, Cr or mixture thereof; and
D is Mo, W, V or mixture thereof;
and wherein
a=0.1–10;
c=6–18;
n is the number of acidic hydrogens in the catalyst, and is a number greater than 1;
y is the number of oxygens in the catalyst, and is a number ranging from about 10 to 70; and
x is the moles of water of crystallization, and is a number ranging from 0 to about 40.

Using the process of the invention, high yields of methyl-t-butyl ether and other t-alkyl methyl ethers are obtained with very desirable low concentrations of by-product dimethyl ether.

The central aspect of the present invention is the use of the particular catalysts noted in the formula above in the liquid phase reaction of isobutylene or of a tertiary olefin and methanol to give methyl-t-alkyl ether. The tertiary olefin has the formula $RHC=CR_2^1$ wherein R is H or an alkyl and $R^1$ is alkyl. The catalysts are suitably any of those catalysts delimited by the formula above. In a preferred embodiment, the molybdenum, tungsten and vanadium are employed separately. This is conveniently accomplished in the formula by setting D separately equal to molybdenum, tungsten or vanadium. Of special interest in the present invention are those catalysts that contain phosphorus, silicon and germanium.

The number of $H_2O$ molecules contained in the catalyst as water of crystallization can vary widely, depending on the method of preparation and on the after-treatment of the catalyst. Thus in each catalyst "X" may range from zero to about 40. Furthermore, an interaction between the "acidic" hydrogens and the water of crystallization may occur such that the value of "n" is changed. This may occur e.g. upon partial reduction of a catalyst of the above formula.

The catalysts of the invention are prepared by known techniques. Specific preparations of these catalysts are shown in the working examples of this specification. Broadly, however, the catalysts of the invention may be prepared by any of the techniques known in the art.

The catalyst employed in the reaction is suitably employed as a dissolved component of the liquid mixture. Desirable results of the present invention are obtained with the homogeneous liquid mixture because of the substantially greater contacting efficiency.

The concentration of the catalyst in the liquid phase reaction mixture may vary widely. For the homogeneous catalysts, it is most convenient to state the catalyst concentration in terms of weight percent. The weight percent of the catalysts may vary within very broad limits, but it has been found that weight percentages of about 0.1 to about 5% are preferred.

The process conditions for the liquid phase reaction may vary widely, but in normal practice, the temperature ranges from about 10° to 200° C. and the reaction is normally conducted under atmospheric or superatmospheric pressure. Of special interest in the process of the invention are reactions conducted at temperatures of 70° to 150° C. using superatmospheric pressure. The contact time of these reaction conditions will vary substantially. The contact time may range from as low as a few seconds to a number of hours depending upon the state of the catalyst employed, the reaction temperature and the pressure. The molar ratio of the tertiary olefin to methanol may vary widely so long as the predominant product is the tertiary alkyl methyl ether. Suitably, the molar ratios are about 0.3 to about 10 moles of methanol per mole of olefin.

In addition to these process variables, other modifications of the reaction may be used. For example, a suitable solvent may be employed that will not deleteriously affect the reaction and that is conveniently removed from the reaction product. The reaction is suitably conducted in any reactor that can accommodate a liquid phase reaction. Thus, a stirred and heated pressure vessel containing the reactants with the catalyst dissolved in them may be used for a commercial batch operation. In a continuous operation, the reactants with the catalyst dissolved may be passed through a heated tubular reactor (packed with inert material for improved heat transfer) such that the product, and any unreacted material, are continuously removed.

SPECIFIC EMBODIMENTS

EXAMPLES 1–8

Preparation of methyl-t-butyl ether using various catalysts

The heteropoly acids used as catalysts of this invention were prepared by mixing solutions of theoretical amounts of a soluble molybdate or tungstate with a salt solution containing the hetero atom followed by acidifying, heating, extracting the heteropoly acid with ether, then crystallizing from the ether solution.

$H_4GeW_{12}O_{40}.XH_2O$ used in Example 12 was prepared as follows:

A solution A was prepared by stirring and heating 3.9 g. powdered $GeO_2$ (37 millimoles) and 14.2 g. of 50% aqueous NaOH (178 milliequivalents) in 100 ml. water.

A solution B was made by dissolving 159 g. $Na_2WO_4.2H_2O$ (482 millimoles) in 400 ml. cold water, and adding approximately 80 ml. of 15% hydrochloric acid, with stirring, until the pH value of the solution became 6.8-7.0.

Solutions A and B were combined, stirred and heated. The pH value was adjusted to about 3 with 65 ml. additional 15% HCl, then 20 ml. 30% HCl was added in portions. The solution was boiled for two hours and allowed to evaporate to about 400 ml. residual volume. The mixture was then cooled in an ice-bath to 18° C., mixed with 50 ml. concentrated HCl, and poured through a filter into a separating funnel, followed by addition of 250 ml. ether in portions, with intermittent shaking. Another 50 ml. concentrated HCl was added, the mixture shaken, then allowed to separate. Three liquid layers separated, the lowest layer contained the product heteropoly acid dissolved in ether. It was separated, filtered and the ether evaporated in a water bath at 50° C. The residual solid was dissolved in 80 ml. water, filtered, mixed with 20 ml. concentrated HCl, and the extraction with ether was repeated as above. The ether extract was mixed with 50 ml. water, the ether removed by evaporation, and the concentrated solution slowly evaporated to dryness in a vacuum dessiccator. The white, crystalline solid thus obtained weighed 77 g. The other catalysts of the Table were prepared in essentially the same manner.

The catalysts were used to prepare methyl-t-butyl ether in a one-liter laboratory pressure reaction vessel equipped with a stirrer, charging ports, a thermocouple, a pressure gage and a blowout disc.

The procedure used in Example 1 of the Table was as follows:

The catalyst $H_4SiMo_{12}O_{40}.XH_2O$ (0.9 g.) was charged to the pressure vessel, the vessel was closed and evacuated. A mixture of 56 g. isobutylene (1 mole) and 128 g. methanol (4 moles), confined under its own vapor pressure in a small steel bomb, was charged to the reaction vessel by suction, through one of the charging ports. The reaction vessel was then heated with agitation at 135° C. for one hour. The pressure in the vessel rose initially to 220 p.s.i., then decreased to 150 p.s.i. The catalyst was completely soluble in the reaction mixture. After the reaction, the reaction vessel was cooled to 0° C. and the reaction mixture was analyzed by gas chromatography. The catalysts, catalyst concentrations, molar ratios of reactants and results are shown in the following Table.

The results of these reactions are given in the Table where the conversion and selectivity are defined as follows:

$$\% \text{ conversion} = \frac{\text{moles of reactant reacted} \times 100}{\text{moles of reactant charged}}$$

$$\% \text{ selectivity} = \frac{\text{moles of methyl-t-butyl ether obtained}}{\text{moles of isobutylene reacted}}$$

Also included as a part of the results is the amount of by-product dimethyl ether that is formed. This result is expressed in terms of the percent of charged methanol that is converted to dimethyl ether.

TABLE

Liquid Phase Synthesis of Methyl-t-Butyl Ether Using Various Catalysts

| | | | | Mole % Conversion | | Results % Selectivity to Methyl-t- | % $CH_3OH$ to |
|---|---|---|---|---|---|---|---|
| Example | Catalyst | Catalyst Conc. Wt. % | $CH_3OH/iC_4=$ | $i-C_4=$ | $CH_3OH$ | Butyl Ether | Dimethyl Ether |
| 1 | $H_4SiMo_{12}O_{40} . XH_2O$ | 0.5 | 4 | 81.5 | 20.8 | 100.0 | 0.2 |
| 2 | " | 0.5 | 3 | 81.5 | 27.9 | 100.0 | 0.2 |
| 3[a] | " | 0.5 | 3 | 82.2 | 26.8 | 99.2 | n.d.[b] |
| 4 | " | 0.5 | 1 | 66.2 | 61.6 | 98.2 | n.d. |
| 5 | $H_4GeMo_{12}O_{40} . XH_2O$ | 0.5 | 1 | 66.2 | 66.4 | 100.6 | n.d. |
| 6 | $H_3PMo_{12}O_{40} . XH_2O$ | 0.5 | 1 | 70.8 | 63.0 | 88.4 | <0.2 |
| 7 | " | 0.5 | 4 | 67.3 | 16.2 | 92.8 | n.d. |
| 8 | $H_4PVMo_{11}O_{40} . XH_2O$ | 0.5 | 4 | 30.6 | 6.5 | 95.9 | 0 |
| 9 | " | 2.0 | 4 | 82.5 | 21.0 | 98.1 | 0.7 |
| 10 | " | 0.5 | 1 | 65.0 | 64.7 | 99.2 | <0.2 |
| 11 | $H_4SiW_{12}O_{40} . XH_2O$ | 0.5 | 1 | 76.7 | 56.9 | 73.8 | <0.5 |
| 12 | $H_4GeW_{12}O_{40} . XH_2O$ | 0.5 | 1 | 73.7 | 57.8 | 78.7 | <0.5 |
| 13 | $H_3PW_{12}O_{40} . XH_2O$ | 0.5 | 1 | 76.0 | 55.5 | 74.7 | <0.5 |
| 14 | " | 0.5 | 4 | 66.6 | 15.8 | 97.5 | 0.5 |
| 15 | " | 1.0 | 3 | 81.4 | 27.8 | 96.3 | 1.6 |
| 16 | " | 1.0 | 4 | 83.5 | 24.3 | 100.0 | n.d. |
| 17 | " | 2.0 | 4 | 81.7 | 21.4 | 90.6 | 0.5 |
| 18[c] | " | 2.0 | 4 | 88.0 | 24.4 | 93.0 | 0.5 |

[a] temp. 110° C.
[b] not detected
[c] temp. 102° C.; time 2 hrs.

It is seen from the above data that the production of methyl-t-butyl ether using the catalysts of the invention gives high conversion of the isobutylene at very high selectivity. It is also seen from the data that the yield of dimethyl ether is maintained within a very desirable low range.

EXAMPLE 19

Preparation of t-amyl methyl ether

Using the procedure of Example 1, 100 g. 2-methylbutene-2 (1.43 mole) and 46 g. methanol (1.43 mole) were reacted for 90 minutes at 135° C., in the presence of 0.5 wt.% (0.73 g.) of $H_4SiMO_{12}O_{40}.XH_2O$ as catalyst. The catalyst was soluble in the reaction mixture.

The conversion of the olefin was 34.4%, that of methanol was 28.4%. The product contained 28.2% wt.% of t-amyl methyl ether; the selectivity based on converted 2-methylbutene-2 was 80.2%.

EXAMPLE 20

Preparation of t-amyl methyl ether

Using the procedure of Example 1, 70 g. 2-methylbutene-2 (1.0 mole) was reacted with 96 g. methanol (3.0 moles) for 90 minutes at 135° C., in the presence of 1.0 wt.% (1.7 g.) of $H_4SiMo_{12}O_{40} \cdot XH_2O$. The conversion of the olefin was 46.0%, that of methanol 14.6%. The product contained 28 wt.% of t-amyl methyl ether; the selectivity based on converted 2-methylbutene-2 was 95%.

We claim:

1. A process for the preparation of methyl-t-alkyl ethers comprising reacting a mixture of tertiary olefin of the formula $RHC=CR_2^1$, wherein R is H or alkyl and $R^1$ is alkyl, and methanol in the liquid phase in the presence of a homogeneous, free-heteropoly acid catalyst having the formula:

$$H_n A_a D_c O_y \cdot XH_2O$$

wherein

A is P, B, Si, Ge, Sn, As, Sb, U, Mn, Re, Cu, Ni, Co, Fe, Ce, Th, Cr or mixture thereof; and D is Mo, W, V or mixture thereof; and wherein $a = 0.1-10$;

$c = 6-18$;

n is the number of acidic hydrogens in the catalyst, and is a number greater than one;

y is the number of oxygens in the catalysts, and is a number ranging from about 10 to 70; and x is the moles of water of crystallization and is a number ranging from 0 to about 40.

2. The process of claim 1 wherein D is Mo.
3. The process of claim 1 wherein D is W.
4. The process of claim 1 wherein D is V.
5. The process of claim 1 wherein A is P.
6. The process of claim 1 wherein A is Si.
7. The process of claim 1 wherein A is Ge.
8. The process of claim 1 wherein the catalyst is $H_4SiMo_{12}O_{40} \cdot XH_2O$.
9. The process of claim 1 wherein the reaction is conducted at a temperature of 10°–200° C.
10. The process of claim 1 wherein isobutylene is reacted.

* * * * *